US006232529B1

(12) United States Patent
Singletary et al.

(10) Patent No.: US 6,232,529 B1
(45) Date of Patent: *May 15, 2001

(54) METHODS OF PRODUCING HIGH-OIL SEED BY MODIFICATION OF STARCH LEVELS

(75) Inventors: George Singletary, Ankeny; Paul C. Anderson, West Des Moines; Sean J. Coughlan, Des Moines, all of IA (US)

(73) Assignee: Pioneer Hi-Bred International, Inc., Des Moines, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/752,503

(22) Filed: Nov. 20, 1996

(51) Int. Cl.$^7$ ................................. A01H 1/00; A01H 5/10
(52) U.S. Cl. ..................... 800/281; 800/263; 800/264; 800/276; 800/284; 800/287; 800/320.1
(58) Field of Search ............................. 435/172.3, 172.1; 800/205, 255, 250, 230, 235, DIG. 56, 263, 264, 276, 281, 284, 287, 320.1

(56) References Cited

U.S. PATENT DOCUMENTS

| | | | |
|---|---|---|---|
| 5,498,830 | * 3/1996 | Barry et al. ........................ | 800/205 |
| 5,981,840 | * 11/1999 | Zhao et al. ........................ | 800/294 |
| 5,990,390 | * 11/1999 | Lundquist et al. ................. | 800/302 |
| 6,057,493 | 5/2000 | Willmitzer et al. ................ | 800/284 |

FOREIGN PATENT DOCUMENTS

| | | | |
|---|---|---|---|
| 0 634 491 A1 | 1/1995 | (EP) | C12N/15/82 |
| WO 94/29467 | 12/1994 | (WO) | C12N/15/82 |
| WO 96/02652 | 2/1996 | (WO) | C12N/15/53 |
| WO 9911805 | 3/1999 | (WO) . | |

OTHER PUBLICATIONS

Kobmann et al. "Transgenic plants as a tool to understand starch biosynthesis." In Carbohydrate Bioengineering, ed. S.B. Pedersen et al, Elsevier Science B.V, Progress in Biotechnol vol. 10, pp. 217–278, 1995.*
Herbers et al., "Manipulating metabolic partitioning in transgenic plants", *Trends in Biotechnology*, 14: 198–205, 1996.
Murphy, D.J., "Engineering oil production in rapeseed and other oil crops", *Trends in Biotechnology*, 14: 206–212, 1996.
Singletary et al., "Influence of Gene Dosage on Carbohydrate Synthesis and Enzymatic Activities in Endosperm of Starch–Deficient Mutants of Maize", *Plant Physiology*, 113: 293–304, 1997.
Bettey et al., "Nature of the effect of the r locus on the lipid content of embryos of peas (*Pisum sativum* L.)"; *Planta*; vol. 180; pp. 420–428; (1990).

Wang et al., "An Analysis of Seed Development in *Pisum sativum*. XIII. The Chemical Induction of Storage Product Mutants"; *Plant Breeding*; vol. 105; pp. 311–320; (1990).
Coxon et al., "The Effect of the $r_a$ and $r_b$ Loci on the Lipid Content of the Seed of *Pisum sativum*"; *Theor. Appl. Genet.*; vol. 64; pp. 47–50; (1992).
Shewry et al., "Protein Metabolism in Developing Endosperms of High–Lysine and Normal Barley"; *Cereal Chemistry*; vol. 56(2); pp. 110–117; (1979).
Miflin et al., "The Synthesis of Proteins in Normal and High Lysine Barley Seeds"; Biochemistry Department, Rothamsted Experimental Station, Harpenden, Herts., England; pp. 239–273.
Earle, F.R., et al, "Composition of the Component Parts of the Corn Kernel"; Cereal Chem.; vol. 23(5); pp. 504–511; (1946).
Anderson, R.A. and S.A. Watson, "The Corn Milling Industry"; *CRC Handbook of Processing and Utilization in Agriculture*; I.A. Wolff, Boca Raton, FL, CRC Press, Inc.; vol. 2(1); pp. 31–61; (1982).
Doehlert, D.C. and R.J. Lambert, "Metabolic Characteristics Associated with Starch, Protein, and Oil Deposition in Developing Maize Kernals"; *Crop Sci.*; vol. 31; pp. 151–157; (1991).
Hannah, L.C., et al., "Biotechnological Modification of Carbohydrates for Sweet Corn and Maize Improvement"; *Sci. Horticult.*; vol. 55; pp. 177–197; (1993).
Smith, A.M and C. Martin, "Starch Biosynthesis and the Potential for its Manipulation"; *Biosyn. and Manipulation of Plant Prod.*; D. Grierson; vol. 3; pp. 1–54; (1993).
Visser, R.G.F. and E. Jacob, "Towards Modifying Plants for Altered Starch Content and Composition"; *Trends In Biotech.*; vol. 11; pp. 63–68; (1993).
Muller–Rober, B. and J. Koβmann, "Approaches to Influence Starch Quantity and Starch Quality in Transgenic Plants"; *Plant, Cell and Environ.*; vol. 17; pp. 601–613; (1994).
Bhullar, S.S., "Bioregulation of Starch Accumulation in Developing Seeds"; *Current Sci.*; vol. 68(5); pp. 507–516; (1995).
Morell, M.K., et al., "The Biochemistry and Molecular Biology of Starch Synthesis in Cereals"; *Aust. J. Plant Physiol.*; vol. 22; pp. 647–660; (1995).
Nelson, O. and D. Pan, "Starch Synthesis in Maize Endosperms"; *Plant Physiol.*; vol. 46; pp. 475–496; (1995).

(List continued on next page.)

*Primary Examiner*—Mary E. Mosher
(74) *Attorney, Agent, or Firm*—Pioneer Hi-Bred International, Inc.

(57) ABSTRACT

The present invention provides methods of obtaining a greater than normal concentration of oil in the seed of a plant, the method comprising altering the carbon metabolism in the seed leading to an alteration in the partitioning of assimilates from starch biosynthesis to enhance the biosynthesis and accumulation of oil, preferably without significantly affecting the size of the storage organ in a way that adversely impacts the commercial value of the material. Seeds produced by the present methods are also provided.

6 Claims, 1 Drawing Sheet

OTHER PUBLICATIONS

Wasserman, B.P., et al., "Biotechnology: Progress Toward Genetically Modified Starches"; *Cereal Foods World*; vol. 40(11); pp. 810–817; (1995).

Singh, D.G., et al., "β–Glucosylarginine: a New Glucose–Protein Bond in Self–glucosylating Protein from Sweet Corn"; *FEBS Lett.*; vol. 376; pp. 61–64; (1995).

Cao, H., et al., "Btl, a Structural Gene for the Major 39–44 kDa Amyloplast Membrane Polypeptides"; *Physiol. Plant*; vol. 95(2); pp. 177–186; (1995).

Shannon, J.C., et al., "Nucleotides and Nucleotide Sugars in Developing Maize Endosperms: Synthesis of ADP–glucose in Brittle–1"; *Plant Physiol.*; vol. 110(3); pp. 835–843; (1996).

Weig, A. and E. Komor, "An Active Sucrose Carrier (Scrl) that is Predominantly Expressed in the Seedlings of *Ricinus communis* L."; *J. of Plant Physiol.*; vol. 147(6); pp. 685–690; (1996).

Fitzpatrick, L.M. and T. ap Rees, "The Hexose Translocator of the Chloroplast Envelope"; *J. Exp. Bot.*; vol. 47; p. 77; (1996).

Giroux, M.J. and L.C. Hannah, "ADP–glucose Phyrophosphorylase in Shrunken–2 and Brittle–2 Mutants of Maize"; *Mol. Gen. Genet.*; vol. 243; pp. 400–408; (1994).

Hylton, C. and A.M. Smith, "The rb Mutation of Peas Causes Structural and Regulatory Changes in ADP–glucose Pyrophosphorylase from Developing Embryos"; *Plant Physiol.*; vol. 99; pp. 1626–1634; (1992).

Neuhaus, H.E. and M. Stitt, "Control Analysis of Photosynthate Partitioning: Impact of Reduced Activity of ADP–glucose Pyrophosphorylase or Plastid Phosphoglucomutase on the Fluxes to Starch and Sucrose in Arabidopsis thaliana (L.) Heynh"; *Planta*; vol. 182; pp. 445–454; (1990).

Muller–Rober, B., et al., "Inhibition of the ADP–Glucose Pyrophosphorylase in Transgenic Potatoes Leads to Sugar–Storing Tubers and Influences Tuber Formation and Expression of Tuber Storage Protein Genes"; *EMBO Journal*; vol. 11(4); pp. 1229–1238; (1992).

Smith–White, B.J. and J. Preiss, "Comparison of Proteins of ADP–Glucose Pyrophosphorylase from Diverse Sources"; *J. Mol. Evol.*; vol. 34; pp. 449–464; (1992).

Bae, J.M., et al., "Cloning and Characterization of the Brittle–2 Gene of Maize"; *Maydica*; vol. 35; pp. 317–322; (1990).

Bhave, M.R., et al., "Identification nad Molecular Characterization of Shrunken–2 cDNA Clones of Maize"; *Plant Cell*; vol. 2; pp. 581–588; (1990).

Giroux, M., et al., "The Large Subunit of the Embryo Isoform of ADP Glucose Pyrophosphorylase from Maize"; *Plant Physiol.*; vol. 108; pp. 1333–1334; (1995).

Preiss, J., "Biosynthesis of Starch: ADPglucose Pyrophosphorylase, the Regulatory Enzyme of Starch Synthesis: Structure–Function Relationships"; *Denpun Kagaku*; vol.40(2); pp. 117–131; (1993).

Stark, D.M., et al., "Regulation of the Amount of Starch in Plant Tissues by ADP Glucose Pyrophosphorylase"; *Science*; vol. 258; pp. 287–292; (1992).

Giroux, M.J., et al., "A Single Gene Mutation that Increases Maize Seed Weight"; *Proc. Natl. Acad. Sci.*; vol. 93; pp. 5824–5829; (1996).

Kleczkowski, L.A., et al., "Insensitivity of Barley Endosperm ADP–Glucose Pyrophosphorylase to 3–Phosphoglycerate and Orthophosphate Regulation"; *Plant Physiol.*; vol. 101; pp. 179–186; (1993).

Adkins, G.K. and C.T. Greenwood, "The Isolation of Cereal Starches in the Laboratory"; *Die Starke*; vol. 7; pp. 213–218; (1966).

Lee, E.Y.C., "Multiple Forms of 1,4–α–Glucan Phosphorylase in Sweet Corn"; *FEBS Lett.*; vol. 27(2); pp. 341–345; (1972).

Doehlert, D.C., et al., "Enzymes of Sucrose and Hexose Metabolism in Developing Kernels of Two Inbreds of Maize"; *Plant Physiol.*; vol. 86; pp. 1013–1019; (1988).

Tsai, C. and O. Nelson, "Starch–Deficient Maize Mutant Lacking Adenosine Diphosphate Glucose Pyrophosphorylase Activity", *Science*; vol. 151; pp. 341–343; (1966).

Dickinson, D.B. and J. Preiss, "Presence of ADP–Glucose Pyrophosphorylase in Shrunken–2 and Brittle–2 Mutants of Maize Endosperm"; *Plant Physiol.*; vol. 44; pp. 1058–1062; (1969).

Prioul, J.L., et al., "Expression of ADP–Glucose Pyrophosphorylase in Maize (Zea mays L.) Grain and Source Leaf During Grain Filling"; *Plant Physiol.*; vol. 104; pp. 179–187; (1994).

Styer, R.C. and D.J. Cantliffe, "Dependence of Seed Vigor During Germination on Carbohydrate Source in Endosperm Mutants of Maize"; *Plant Physiol.*; vol. 76; pp. 196–200; (1984).

Finnegan, J., and D. McElroy, "Transgene Inactivation: Plants Fight Back!"; *Bio/Technology*; vol. 12; pp. 883–888; (1994).

Matzke, M.A. and A.J.M. Matzke, "How and Why Do Plants Inactivate Homologous (Trans)genes?"; *Plant Physiol.*; vol. 107; pp. 679–685; (1995).

Bird, C.R. and J.A. Ray, "Manipulation of Plant Gene Expression by Antisense RNA"; *Biotech and Gen. Eng. Rev.*; vol. 9; pp. 207–227; (1991).

Steup, M., "Starch Degrading Enzymes"; *Methods in Plant Biochemistry*; Academic Press; vol. 3; pp. 103–128; (1990).

Creighton, T.E., "Proteins—Structures and Molecular Properties", Second Ed.; Freeman & Co., New York; pp. 442–452; (1993).

Kim, W.T., et al., "Immunocytochemical Localization of ADPglucose Pyrophosphorylase in Developing Potato Tuber Cells"; *Plant Physiol.*; vol. 91; pp. 217–220; (1989).

Miller, M.E., and P.S. Chourey, "Intracellular Immunolocalization of Adenosine 5'–diphosphoglucose Pyrophosphorylase in Developing Endosperm Cells of Maize (Zea mays L.)"; *Planta*; vol. 197; pp. 522–527; (1995).

Ardila, F.J. and J.S. Tandecarz, "Potato Tuber UDP–Glucose: Protein Transglucosylase Catalyzes its own Glucosylation"; *Plant Physiol.*; vol. 99; pp. 1342–1347; (1992).

Lomako, J., et al., "A Self–glucosylating Protein is the Primer for Rabbit Muscle Glycogen Biosynthesis"; *FASEB J.*; vol. 2; pp. 3097–3103; (1988).

Cao, H., et al., "Btl, a Structural Gene for the Major 39–44 kDa Amyloplast Membrane Polypeptides"; *Physiol. Plant.*; vol. 18; pp. 176–186; (1995).

Boyer, C.D. and L.C. Hannah, "Kernel Mutants of Corn"; *Specialty Corns*; A.R. Hallauer, Boca Raton CRC Press, Inc.; pp. 1–28; (1994).

Denyer, K, et al., "The Isolation and Characterization of Novel Low–Amylose Mutants of *Pisum sativum* L." *Plant, Cell and Environ.*; vol. 18; pp. 1019–1026; (1995).

Luthra, R., et al., "Relationship of Carbohydrate Metabolism with Lipid Biosynthesis in Developing Sunflower (Helianthus annuus L.)"; *J. Plant Physiol.*; vol. 137; pp. 312–318; (1991).

Yazdi–Samadi, B., et al., "Components of Developing Soybean Seeds: Oil, Protein, Sugars, Starch, Organic Acids, and Amino Acids"; *Agron. J.*; vol. 69; pp. 481–486; (1977).

Norton, G. and J.F. Harris, "Compositional Changes in Developing Rape Seed (*Brassica napus* L.)"; *Planta* (Berl.); vol. 123; pp. 163–174; (1975).

Armstromg, C.L., et al., "Development and Availability of Germplasm with High Type II Culture Formation Response", *Maize Genetics Cooperation Newsletter*; vol. 65; pp. 92–93; (1991).

Chu, C., et al., "Establishment of an Efficient Medium for Anther Culture of Rice Through Comparative Experiments on the Nitrogen Sources"; *Scientia Sinica*; (Peking); vol. 18(5); pp. 659–668; (1975).

Eriksson, T., "Studies on the Growth Requirements and Growth Measurements of Cell Cultures of *Haplopappus gracilis*"; *Physiol. Plant.*; vol. 18; pp. 976–993; (1965).

Murashige, T. and F. Skoog, "A Revised Medium for Rapid Growth and Bio Assays with Tobacco Tissue Cultures"; *Physiol. Plant.*; vol. 15; pp. 473–497; (1962).

Singletary, G.W. and F.E. Below, "Nitrogen–Induced Changes in the Growth and Metabolism of Developing Maize Kernels Grown in Vitro", *Plant Physiol.*; vol. 92; pp. 160–167; (1990).

McCleary, B.V., et al., "Quantitative Measurement of Total Starch in Cereal Flours and Products"; *J. of Cereal Sci.*; vol. 20; pp. 51–58; (1994).

Jones, M.G.K., et al., "Enzymic Assay of $10^{-7}$ to $10^{-14}$ Moles of Sucrose in Plant Tissues"; *Plant Physiol.*; vol. 60; pp. 379–383; (1977).

\* cited by examiner

METHODS OF PRODUCING HIGH-OIL SEED BY MODIFICATION OF STARCH LEVELS

TECHNICAL FIELD

The present invention relates generally to modifying seed composition. Specifically, the present invention relates to increasing the concentration of oil in seed.

BACKGROUND OF THE INVENTION

On average, 20% of corn produced in the U.S. is used for domestic food and industrial purposes including wet milling. In 1995, American farmers produced 7.4 billion bushels of corn, 20.6% of which was refined by the corn wet milling industry into more than 51 billion pounds of product.

Material output from the corn wet milling process includes starch for direct use or chemical modification, starch used as a degradative feedstock for the manufacture of an abundance of ancillary products, and coproducts/byproducts such as gluten feed, gluten meal and corn oil. As the list of products containing corn derived ingredients grows, so does the percentage of the U.S. crop that is utilized by the wet milling industry.

The central component critical in the direct, or indirect, use of corn for many products is starch. Interestingly, however, in some instances the unit value of coproducts exceeds that of starch. Such is the case with corn oil, having a value of approximately $0.23/lb, compared to $0.126/lb for starch (ERS 1995; ERS 1995). Corn wet millers rely on credits obtained from coproduct isolation and sale to minimize the net cost of the corn they grind for starch recovery. The monetary value realized by the isolation and sale of oil, or oil containing products (e.g., dry germ), is an important portion of these coproduct credits. Furthermore, because of the high unit value of oil, the coproduct credit for this material is more sensitive to changes in refining yield than all other coproducts.

In recognizing the importance and value of constituents isolated from grain in the wet milling process, it is useful to be aware of the starting composition of the grain and its parts. On a whole grain dry weight basis (db), corn is composed of the following primary constituents of economic importance: 4.0% oil, 9.7% protein, 69.8% starch, 3.5% sugars and 5.9% fiber. Similarly, the average composition of component parts of unprocessed grain is as follows: (1) the germ (defined as the organ inclusive of the scutellum and embryo proper) comprises 11.9% of the whole kernel and contains 34% oil, 8.2% starch, 18.8% protein, 10.8% sugar and 10.1% ash, and (2) the endosperm comprises 82% of the whole kernel and contains 86% starch, 9.4% protein, 0.8% oil and 0.6% sugar (Earle, F. R., J. J. Curtis, et al., "Composition of the Component Parts of the Corn Kernel"; *Cereal Chem.;* Vol. 23(5); pp. 504–511; 1946; incorporated herein in its entirety by reference). By calculation, Earle, et al., (1946), have determined that 84% of the seed oil is found in the germ and 98% of the kernel starch is located in the endosperm.

The purpose of the wet milling process is to fractionate the kernel and isolate chemical constituents of economic value into their component parts. This pertains specifically to starch, which is fractionated into a highly purified form. Other materials are typically isolated in crude forms (e.g., unrefined oil) or as a wide mix of materials which commonly receive little to no additional processing beyond drying. Hence, in the wet milling process grain is softened by steeping and cracked by grinding to release the germ from the kernels. The germ is separated from the heavier density mixture of starch, hulls and fiber by "floating" the germ segments free of the other substances in a centrifugation process. This allows a clean separation of the oil-bearing fraction of the grain from tissue fragments that contain the bulk of the starch. Since it is not economical to extract oil on a small scale, many wet milling plants ship their germ to large, centralized oil production facilities. Oil is expelled or extracted with solvents from dried germs and the remaining germ meal is commonly mixed into corn gluten feed (CGF), a coproduct of wet milling. Typical composition of spent germ cake, the germ material remaining after oil is extracted, is 20% starch, 25% protein, 1% fat, 10% crude fiber and 25% pentosans (Anderson, R. A. and S. A. Watson, "The Corn Milling Industry"; *CRC Handbook of Processing and Utilization in Agriculture;* A. Wolff, Boca Raton, Fla., CRC Press, Inc.; Vol. 11; Part 1; *Plant Products:* 31–61; 1982; incorporated herein in its entirety by reference). Hence, starch contained within the germ is not recovered as such in the wet milling process and is channeled to CGF. The unit value of CGF is roughly 20% that of corn oil and 50% that of corn starch. While increasing the oil content in seed, it is desirable that endosperm size and hence, starch content not be reduced because it is helpful if starch revenues are also maintained.

Current research indicates that genetic selection in maize can lead to increased oil content in the embryo, but that the resultant genotype is associated with reduced starch production. See e.g. Doehlert and Lanibert, "Metabolic Characteristics Associated with Starch, Protein, and Oil Deposition in Developing Maize Kennels"; *Crop Sci.;* Vol. 32; pp. 151–157; (1991); incorporated herein in its entirety by reference.

The central importance of starch to plant development and to food, feed, and industrial markets has motivated researchers across many years to look for mechanisms which control starch biosynthesis. Mutants of maize which affect seed starch deposition have been instrumental in characterizing the biochemistry of starch synthesis. Considerable research effort continues to explore the metabolic systems involved in synthesizing starch, but in addition molecular techniques are being used to dissect genes which encode enzymes known to be critical in starch biosynthesis. In discovering which regions of the genes encode metabolism-controlling aspects of the enzymes, scientists are beginning to manipulate starch metabolism through genetic engineering. Interest in controlling starch biosynthesis through molecular and genetic techniques has intensified significantly in recent years and several recent reviews describe fundamental aspects of starch biosynthesis and/or how they may be manipulated in transgenic plants, see e.g. Hannah, L. C., M. Giroux et al, "Biotechnological Modification of Carbohydrates for Sweet Corn and Maize Improvement"; *Scientia Horticulturae;* Vol. 55; pp. 177–197; 1993; Smith, A. M. and C. Martin, "Starch Biosynthesis and the Potential for its Manipulation"; *Biosyn. And Manipulation of Plant Products;* D. Grierson; Vol. 3; pp. 1–54; 1993; Visser, R. G. F. and E. Jacob, "Towards Modifying Plants for Altered Starch Content and Composition"; *Trends In Biotechnology;* Vol. 11; pp. 63–68; 1993; Muller-Rober, B. and J. Kossmann, "Approaches to Influence Starch Quantity and Starch Quality in Transgenic Plants"; *Plant Cell Environ.;* Vol. 17; pp. 601–613; 1994; Bhullar, S. S., "Bioregulation of Starch Accumulation in Developing Seeds"; *Current Science;* Vol. 68(5); pp. 507–516; 1995; Morell, M. K., S. Rahan, et al., "The Biochemistry and Molecular Biology of Starch Synthesis in Cereals"; *Aust. J. Plant Physiol.;* Vol. 647–660; 1995;

Nelson, O. and D. Pan, "Starch Synthesis in Maize Endosperms"; *Plant Physiol.;* Vol. 46; pp. 475–496; 1995; Wasserman, et al., "Biotechnology: Progress Toward Genetically Modified Starches" *Cereal Foods World;* Vol. 40(11); pp. 810–817; 1995; all incorporated herein in its entirety by reference.

Sucrose is considered to be the primary metabolite utilized in the synthesis of starch, although seed grown in vitro with the reducing sugars, glucose or fructose, also produce starch. In simple terms, the sugars are converted into the sugar nucleotides, ADP-glucose and UDP-glucose, either directly or via phosphorylated carbohydrate intermediates. The sugar nucleotides are substrates for the synthase enzymes which polymerize the glucosyl portion of the molecules into long chains of glucose. The polymers remain essentially linear (amylose) or become branched (amylopectin) and combine in a specific fashion to become granules of starch. The mechanism of initiating the synthesis of the glucosyl polymer is not known with certainty, although it is hypothesized that a protein, amylogenin, may serve a nucleating role in the process (Singh, D. G., J. Lomako, et al., "β-glucosylarginine: a New Glucose-Protein Bond in a Self-glucosylating Protein from Sweet Corn"; *FEBS Lett.;* Vol. 376; pp. 61–64; 1995; incorporated herein in its entirety by reference).

The use of seed starch mutants in various crop plants (e.g., corn, pea) and the production of transgenic plants which over- or underexpress specific proteins has indicated that many proteins/enzymes are capable of affecting starch biosynthesis in storage organs. This can occur directly, by impacting the proteins which: (1) produce the substrate(s) for starch synthesis (2) initiate the glucose polymerization process and elongate the structure into macromolecules, or (3) alter the structure of the polymers once the elongation process has begun. Enzymes known, or believed, to participate in these processes include, but are not limited to, ADP-glucose and UDP-glucose pyrophosphorylases, bound and soluble starch eases, starch phosphorylases, starch granule bound and soluble branching enzymes, debranching enzymes, isoamylases and disproportionating enzymes. In addition to a direct impact on starch metabolism, starch production can also be negatively impacted by dysfunction or deficiency of proteins which are catalysts in sugar metabolism or act as transporters of intermediary compounds. Examples of those involved in sugar metabolism include, but are not limited to, sucrose synthases, sucrose phosphate synthase, sucrose phosphate phosphorylase, hexokinases, phosphoglucomutases and phosphoglucoisomerases. Proteins involved in assimilate transport, such as the brittle-1 protein of maize endosperm amyloplast membranes (Cao, H. P., T. D. Sullivan, et al., "Bt1, a Structural Gene for the Major 39–44 kDa Amyloplast Membrane Polypeptides"; *Physiol. Plant;* Vol. 95(2); pp. 177–186; 1995; Shannon, J. C., F. M. Pien, et al., "Nucleotides and Nucleotide Sugars in Developing Maize Endosperms-Synthesis of ADP-glucose in Brittle-1"; *Plant Physiology;* Vol. 110(3); pp. 835–843; 1996; both incorporated herein in its entirety by reference), sucrose carrier proteins (Weig, et al., "An Active Sucrose Carrier (Scr1) that is Predominantly Expressed in the Seedlings of *Ricinus Communis L.*"; *Journal of Plant Physiology;* Vol. 147(6); pp. 685–690; (1990); incorporated herein in its entirety by reference) or others homologous to the hexose transporter of the chloroplast (Fitzpatrick, et al., "The Hexose Translocator of the Chloroplast Envelope"; *J. Exp. Bot.;* Vol. 47; pp. 79; (1996); incorporated herein in its entirety) can also affect starch synthesis by restricting the availability of substrates for normal starch and/or sugar metabolism.

One enzyme which has been shown to be particularly important in starch biosynthesis, as well as in the synthesis of bacterial glycogen, is ADP-glucose pyrophosphorylase (AGP). In bacteria, AGP is a homotetrameric protein, while in plants it is a heterotetrameric complex of two different protein subunits. Dysfunction or absence of either subunit severely reduces starch synthesis. The starch mutants of maize which affect the AGP subunits in the endosperm are brittle-2 (bt2; small subunit) and shrunken-2 (sh2; large subunit) (Giroux, M. and L. Hannah; "ADP-glucose Phyrophosphorylase in Shrunken-2 and Brittle-2 Mutants of Maize"; *Mol. Gen. Genet.;* Vol. 243; pp. 400–408; 1994; incorporated herein in its entirety by reference). The reduction of accumulated starch coincident with lower AGP activity in mutant pea embryo (Hylton. C. and A. M. Smith, "The rb Mutation of Peas Causes Structural and Regulatory Changes in ADP-glucose Pyrophosphorylase from Developing Embryos"; *Plant Physiol.;* Vol. 99; pp. 1626–1634; 1992; incorporated herein in its entirety by reference), Arabidopsis leaf (Neuhaus, H. E. and M. Stitt, "Control Analysis of Photosynthate Partitioning. Impact of Reduced Activity of ADP-glucose Pyrophosphorylase or Plastid Phosphoglucomutase on the Fluxes to Starch and Sucrose in *Arabidopsis thaliana* (L.) Heynh" *Planta;* Vol. 182; pp. 445–454; 1990; incorporated herein in its entirety by reference), or in the tuber of antisensed potato plants (Muller-Rober, B., U. Sonnewald, et al., "Inhibition of the ADP-Glucose Pyrophosphorylase in Transgenic Potatoes Leads to Sugar-Storing Tubers and Influences Tuber Formation and Expression of Tuber Storage Protein Genes"; *EMBO;* Vol. 11(4); pp. 1229–1238; 1992; incorporated herein in its entirety by reference) demonstrates the commanding role of AGP in controlling starch deposition in a wide variety of tissues and plants.

Numerous genes encoding the small and large subunits of AGP from plants have been described (Smith-White, B. J. and J. Preiss, "Comparison of Proteins of ADP-Glucose Pyrophorylase from Diverse Sources"; *J. Mol. Evol.;* Vol. 34; pp. 449–464; 1992; incorporated herein in its entirety by reference). The corresponding genes which have been described for maize are the endosperm specific Bt2 and Sh2 genes (Bae, J. M., M. Giroux, et al., "Cloning and Characterization of the Brittle-2 Gene of Maize"; *Maydica;* Vol. 35; pp. 317–322; 1990; Bhave, M. R, S. Lawrence, et al., "Identification and Molecular Characterization of Shrunken-2 cDNA Clones of Maize"; *Plant Cell;* Vol. 2; pp. 581–588; 1990; incorporated herein in its entirety by reference) and AGP1 (Giroux, M. and B. Smith-White, et al., "The Large Subunit of the Embryo Isoform of ADP Glucose Pyrophosphorylase from Maize"; *Plant Physiol.;* Vol. 108; pp. 1333–1334; 1995; incorporated herein in its entirety by reference). Although referred to as an embryo isoform because of its predominance in the germ of the seed, AGP1 is also expressed in the endosperm (Giroux, M. and L. Hannah, "ADP-Glucose Pyrophosphorylase in Shrunken-2 and Brittle-2 Mutants of Maize"; *Mol. Gen. Genet.;* Vol. 243; pp. 400–408; 1994; incorporated herein in its entirety by reference). AGP1 represents the large subunit of the embryo isoform, whereas AGP2, to-date an uncharacterized gene, corresponds to the small subunit (Giroux and Hannah, 1994).

AGP is an allosteric enzyme and in plants is activated by 3-phosphoglyceric acid (3-PGA) and inhibited by inorganic phosphate (Pi) to varying degrees, depending upon the species and organ source (Preiss, J. "Biosynthesis of Starch: ADP-Glucose Pyrophosphorylase, the Regulatory Enzyme of Starch Synthese: Structure-Function Relationships"; *Den-* pun Kagaku; Vol. 40(2); pp. 117–131; 1993; incorporated herein in its entirety by reference). The importance of the allosteric properties of AGP is recently demonstrated when transgenic plants expressing a bacterial form of AGP (glgC16), which is allosterically "deregulated" compared to the native plant AGP, accumulated 35% more starch than controls (Stark, D. M., K. P. Timmerman, et al., "Regulation of the Amount of Starch in Plant Tissues by ADP-Glucose Pyrophosphorylase"; Science; Vol. 258; pp. 287–292; 1992; incorporated herein in its entirety by reference). Furthermore, allosteric modification of the maize native Sh2 gene can increase seed weight, presumably due, at least in part, to an affect on starch deposition (Giroux, M. J., J. Shaw, et al., "A Single Gene Mutation that Increases Maize Seed Weight"; Proc. Natl. Acad. Sci.; Vol. 93; pp. 5824–5829; 1996; incorporated herein in its entirety by reference). Allosteric variants of AGP, which are less responsive to 3-PGA and Pi are reported to occur naturally in plants (Kleczkowski, L. A., P. Villand, et al., "Insensitivity of Barley Endosperm ADP-Glucose Pyrophosphorylase to 3-Phosphoglycerate and Orthophosphate Regulation"; Plant Physiol.; Vol. 101; pp. 179–186; 1993; incorporated herein in its entirety by reference) and they also can be engineered into plants through gene manipulation and plant transformation.

Because maize germ is known for its oil storing capacity, starch synthesis in this organ has been studied much less than comparable metabolism in the endosperm. Starch granules of the germ are morphologically distinct from those of the endosperm (Adkins, G. K. and C. T. Greenwood, "The Isolation of Cereal Starches in the Laboratory"; Starch; Vol. 7; pp. 213–218; 1966; incorporated herein in its entirety by reference), but in all probability the metabolic differences in endosperm and germ starch biosynthesis are not fundamentally extensive. In fact, many of the enzyme activities important in endosperm sugar and starch metabolism are also very active in the germ (Lee, E. Y. C.; "Multiple Forms of 1,4-a-Glucan Phosphorylase in Sweet Corn"; FEBS Letters; Vol. 27(2); pp. 341–345; 1972; Doehlert, D., T. Kuo, et al., "Enzymes of Sucrose and Hexose Metabolism in Developing Kernels of Two Inbreds of Maize"; Plant Physiol.; Vol. 86; pp. 1013–1019; 1988; both incorporated herein in its entirety by reference). More specifically, AGP activity is known to occur in maize germ (Tsai, C. and O. Nelson, "Starch-Deficient Maize Mutant Lacking Adenosine Diphosphate Glucose Pyrophosphorylase Activity"; Science; Vol. 151; pp. 341–343; 1966; Dickinson, D. B. and J. Preiss, "Presence of ADP-glucose Pyrophosphorylase in Shrunken-2 and Brittle-2 Mutants of Maize Endosperm"; Plant Physiol.; Vol. 44; pp. 1058–1062; 1969; both incorporated herein in their entirety by reference), although it follows a different developmental profile than AGP activity in the endosperm (Prioul, J. L., E. Jeannette, et al., "Expression of ADP-glucose Pyrophosphorylase in Maize (Zea mays L.) Grain and Source Leaf During Grain Filling"; Plant Physiol.; Vol. 104; pp. 179–187; 1994; incorporated herein in its entirety by reference). An analogous situation is expected to occur for starch.

Based on the foregoing, there is a need to provide seed with an increased concentration of coproducts such as oil.

It is therefore an object of the present invention to provide seeds with an increased concentration of oil.

It is a further object of the present invention to provide seeds with an increased concentration of oil compared to the wild type without an increase in seed weight or endosperm size.

It is a further object of the present invention to provide seeds with an increased concentration of oil compared to the wild type.

It is a further object of the present invention to provide methods of producing seeds with an increased concentration of oil without a reduction in endosperm size.

It is a further object of the present invention to provide methods of producing seeds with an increased concentration of oil without an increase in seed weight.

It is a further object of the present invention to provide methods of producing seeds with an increased concentration of oil without the resulting genotype being associated with reduced starch production in the endosperm.

SUMMARY OF THE INVENTION

The present invention provides methods for discriminately disrupting the natural balance between the storage of starch and oil in select plant organs. There is an alteration in partitioning of assimilates from starch biosynthesis to enhance biosynthesis and accumulation of oil. The fundamental outcome is an exchange of composition between starch and oil deposition within the plant organ. Preferably, this is accomplished without affecting the familiar size of the storage organ in a way that significantly affects the ordinary commercial use of the material.

The alteration of seed chemical composition, i.e., higher oil is achieved through inhibition of normal levels of starch biosynthesis. Starch biosynthesis is reduced by a method including but not limited to:

a) co-suppressing an enzyme involved in starch metabolism;

b) antisensing a gene involved in starch metabolism;

c) increasing the expression of a gene responsible for starch breakdown;

d) modifying the activity of an enzyme responsible for starch metabolism;

e) modifying a protein responsible for nucleating starch biosynthesis;

f) modifying a protein responsible for transport of assimilates that feed into the starch biosynthetic pathway;

g) eliminating a gene involved in starch metabolism;

h) mutation of a gene resulting in reduced expression or activity of an enzyme involved in starch biosynthesis, and i) shunting carbon away from starch biosynthesis depriving the pathway of substrates for starch biosynthesis.

The present invention also provides seeds produced by the above methods.

DETAILED DESCRIPTION OF THE INVENTION

Figure 1:
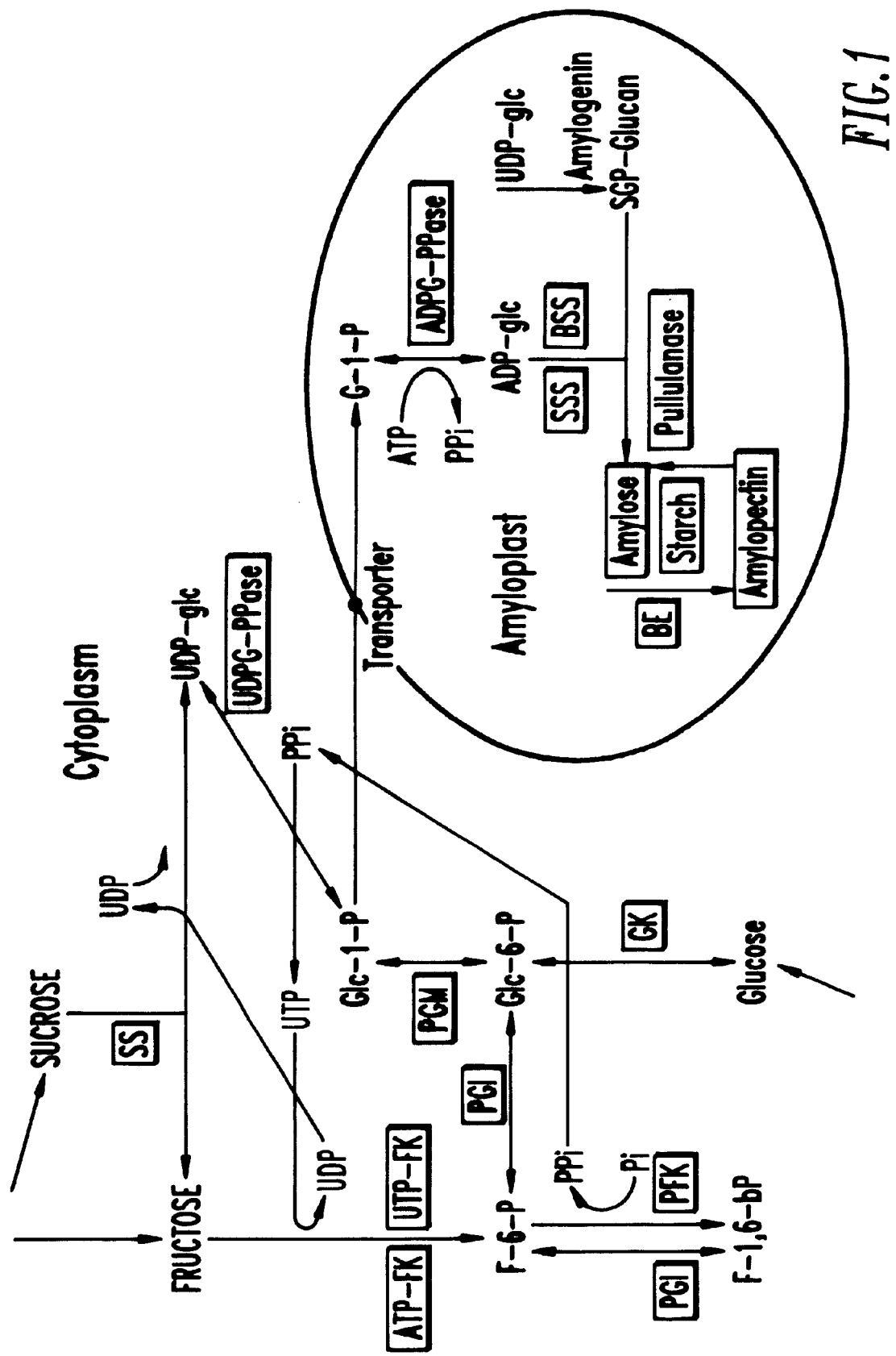
FIG. 1 provides a pathway for starch biosynthesis relevant to the present invention.

It has been unexpectedly discovered that when starch biosynthesis is disrupted in a tissue which ordinarily accumulates a predominance of oil, there will be an enhanced accumulation of oil beyond normal levels. Preferably, this will occur without reduction in size of the storage organ (e.g. seed, germ, scutellum, cotyledon) in a way that has significant impact on the ordinary commercial use of the material as indicated in the art. Enhancing oil accumulation by manipulation of starch synthesis is heretofore undescribed.

As used herein, "starch" means material which is a polymer of glucose and normally comprises amylose, amylopectin or a mixture of these two polymer types. Functionally analogous chemical compounds, also included within the definition of starch, include phytoglycogen (which occurs in select types of corn) and water soluble polysaccharides (glucose polymers lacking the crystalline structure of starch granules).

As used herein "oil" means a constituent or mixture of constituents that in naturally occuring forms are readily soluble in nonpolar solvents such as hexane or diethyl ether, and somewhat soluble in less polar solvents such as aqueous mixtures of alcohols. Oils include neutral lipids, glycolipids, and phospholipids common to the chemical make-up of tissues such as seed of cereals, but especially soybean, sunflower, cottonseed and canola.

Tissue types which ordinarily accumulate a prevalence of oil include seed of oil-bearing crops such as sunflower, cottonseed, soybean and canola and plant tissues of other types of plants such as the germ of cereal crop plants. Cereal seed germ actually includes the embryo proper and the scutellum, but as a whole is rich in oil compared to other materials stored in the organ.

The alteration of seed chemical composition, i.e. higher oil, is achieved in the present invention through inhibition of normal levels of starch biosynthesis. There are a number of enzymes and/or proteins involved in sugar and starch metabolism that interfere with starch biosynthesis. The present invention embodies interfering with starch biosynthesis such that the enzymes and/or proteins involved therein are rendered dysfunctional by way of absence, reduced amount or lessening and/or mitigation of normal catalytic activity. Manipulation of any one or combination of these enzymes and/or proteins for the purpose of restricting starch biosynthesis leads to a counteractive net increase in oil deposition within the tissue, preferably without reduction in endosperm size in cereals such as maize.

The present invention involves seed that contain a greater-than-normal concentration of oil and concomitant lower-than-normal concentration or biosynthesis of starch in the germ or embryo of cereal or oil-bearing seed, respectively. The result is achieved by altering carbon metabolism in the seed Application of the invention pertains to uses of grain that are benefited by an increased concentration of oil in the seed. Examples where commercial advantage would occur with higher-oil grain include: (1) the corn wet milling industry, where increased yield of oil, a high-value coproduct, can significantly impact the profitability of refiners, (2) the oilseed crushing industry, where increased concentration of oil in seed (e.g., soybean, canola) would increase production of oil in the extraction process, and (3) the feed industry, where increased oil results in greater energy density and feed-value of feed material.

In the present invention, the natural balance between the storage of starch and oil is discriminately disrupted in select plant organs. The plant organs of choice are those which normally have a composition which predominates in oil or related lipid materials that commonly serve as a reserve material for plant growth. The principle in concept relies on producing an alteration in partitioning of assimilates from starch biosynthesis to enhanced biosynthesis and accumulation of oil. The fundamental outcome is an exchange of composition between starch and oil deposition within the plant organ. In a preferred embodiment of the present invention, is expected that the interchange of these reserve materials will not affect the familiar size of the storage organ (e.g., seed, germ, scutellum, cotyledons) in a way that has significant impact on the ordinary commercial use of the material.

One embodiment of diminishing starch biosynthesis would be by application of recombinant DNA techniques. Many enzymes important to starch biosynthesis in dicots and monocots have been characterized, at least partially, and ectopic expression of a sense or antisense version of the gene encoding such proteins could lead to absence or dysfunction of the native gene and protein.

Unlike oil-storing seed of dicots, cereal seed contain tissues which are very unlike in their chemical composition. The endosperm is rich in starch and the germ has a predominance of oil. It would be undesirable to negatively affect starch biosynthesis in the endosperm and the intent of this invention is to only impair starch synthesis in tissues which are already high in oil. Hence, in the case of cereal seed or other organs which are heterogeneous in their distribution of oil and starch, it is necessary to select a promoter which only provides gene expression in the tissue rich in oil. The promoter of the maize globulin-1 (glb1) gene is one example where the promoter can restrict gene expression in maize seed to the germ alone. In addition, the glb1 promoter directs the expression of the β-glucuronidase gene more specifically to the scutellum of the germ. This offers a further refinement of the desired application in that the chemical composition of the primary storage tissue of the germ, the scutellum (Styer, R. C. and D. J. Cantliffe, "Dependence of Seed Vigor During Germination on Carbohydrate Source in Endosperm Mutants of Maize"; Plant Physiol.; Vol. 76; pp. 196–200; 1984; incorporated herein in its entirety by reference), can be modified without significantly changing the composition of the embryo proper (i.e., axis).

Starch production is decreased in the present invention pursuant to a method selected from the group consisting of:

a) co-suppressing gene involved in starch metabolism;

b) antisensing a gene involved in starch metabolism;

c) increasing the expression of a gene responsible for starch breakdown;

d) modifying the activity of an enzyme responsible for starch metabolism;

e) modifying a protein responsible for nucleating starch biosynthesis;

f) modifying a protein responsible for nucleating starch biosynthesis;

g) eliminating a gene involved in starch metabolism;

h) mutation of a gene resulting in reduced expression or activity of an enzyme involved in starch biosynthesis; and i) shunting carbon away from starch biosynthesis depriving the pathway of substrates for starch biosynthesis.

Preferably, the method of choice is selected from the group consisting of co-suppressing a gene involved in starch metabolism, antisensing a gene involved in starch metabolism, shunting carbon away from starch biosynthesis and mutation of a gene resulting in reduced expression or activity of a gene involved in starch biosynthesis.

Application of recombinant DNA and plant transformation technologies offers a broad choice of mechanisms for abating starch synthesis. The abatement is achieved by diminishing or abolishing the activity of enzymes important, directly or indirectly, to starch biosynthesis or by like modulation of proteins important in the transport of assimilates required for starch production.

(A) Co-suppression

The general term, homology-dependent gene silencing encompasses the phenomenon of cis-inactivation, trans-inactivation and co-suppression. See Finnegan, et al., "Transgene Inactivation: Plants Fight Back!" *Biotech;* Vol. 12; pp. 883–888; (1994); and Matzke, et al., "How and Why Do Plants Inactivate Homologous (Trans)genes?" *Plant Physiol.;* Vol. 107; pp. 679–685; (1995); both incorporated herein in their entirety by reference. These mechanisms describe cases of gene silencing that involve transgene/transgene or transgene/endogenous gene interactions that lead to reduced expression of protein in plants. In the present case, homology-dependent gene silencing is used to decrease starch synthesis through reduced expression of genes that produce proteins which normally serve as enzymatic catalysts or assimilate transporters involved in starch biosynthesis. Application of any of the mechanisms proposed to function in homology-dependent gene silencing is used to preferably interfere with starch biosynthesis genes including but not limited to sucrose synthase, hexokinase(s), phophoglucomutase, phosphoglucoisomerase, ADP glucose pyrophosphorylase, amylogenin (protein primer of starch biogenesis), soluble and bound starch synthase and starch branching enzymes, starch debranching enzymes, isoamylase enzymes, starch phosphorylases, and the Brittle-1 transport protein.

(B) Antisense

Incorporation of antisense RNA into plants can be used to inhibit the expression of endogenous genes and produce a functional mutation within the genome. The effect is achieved by introducing into the cell(s) DNA which encodes RNA that is complementary to the sequence of mRNA of the target gene. See e.g. Bird, et al., "Manipulation of Plant Gene Expression by Antisense RNA, "*Biotech and Gen. Eng Rev.;* Vol. 9; pp. 207–226; (1991); incorporated herein in its entirety by reference. Manipulation of plant gene expression by antisense RNA is used to preferably interfere with starch biosynthesis genes including but not limited to sucrose synthase, hexokinase(s) phosphoglucomutase, phosphoglucoisomerase, ADP-glucose pyrophosphorylase, amylogenin, soluble and bound starch synthase and starch branching enzymes, starch debranching enzymes, isoamylase enzymes, starch phosphorylases, and the Brittle-1 transport protein.

(C) Elevated Hydrolytic Enzyme Activity

The present invention involves increasing the amount of oil stored in seed by reducing the level of starch biosynthesis and/or accumulation that occurs within the seed. By altering the net distribution of carbon assimilate from deposition as a starch reserve to oil instead, a net accumulation of oil is caused. One mechanism useful in achieving this end is to ensure that there is little or no net accumulation of carbon assimilate into starch, thereby providing these assimilates for the synthesis and deposition of oil. This outcome is achieved by providing enhanced activity of starch degradative enzymes in the tissue targeted for increased oil accumulation. A wide number of enzymes and corresponding isoenzymes are known to a skilled artisan. These enzymes can attack starch or carbohydrate components that may function as precursors of starch molecules and granules, and degrade the material down into intermediary forms that could funnel into mainstream metabolism and be used for the biosynthesis of stored lipids. See e.g. Steup, "Starch Degrading Enzymes"; *Methods in Plant Biochemistry;* Academic Press; Vol. 3; pp. 103–128; (1990); incorporated herein in its entirety by reference. Examples of enzymes which could be expressed in transgenic plants and lead to increased rates of starch degradation (or instability of starch-forming molecules) include, but are not limited to, α-amylase, β-amylase, α-glucosidases and starch phosphorylase.

(D) Modification of the Activity of Enzymes Responsible for Starch Metabolism

One of the predominant ways in which enzyme activity is controlled in cells is by allosteric regulation in which regulatory metabolites bind to regulatory sites on the enzyme. The binding of substrate to one active site can affect the properties of other active sites in the same enzyme molecule. Allosteric regulation by small molecules is profoundly significant in controlling enzymatic activity. For example, two allosteric enzymes that are well understood are the bacterial phosphofructikinase and aspartate transcarbamoylase. See Creighton, T. E., "Proteins Structures and Molecular Properties," Freeman & Co., pp. 444–452; (1993); incorporated herein in its entirety by reference.

AGP is an allosteric enzyme. In plants it is activated by 3-phosphoglyceric acid ("3-PGA") and inhibited by inorganic phosphate (Pi) to varying degrees depending upon the species and organ source. See e.g. Preiss, "Biosynthesis of Starch: ADP Glucose Pyrophosphorylase, the Regulatory Enzyme of Starch Synthesis: Structure-Function Relationships"; *Denpun, Kagaku;* Vol. 40(2); pp. 117–131; (1993); incorporated herein in its entirety by reference.

The importance of the allosteric properties of AGP has recently been demonstrated when transgenic plants expressing a bacterial form of AGP (glgC16), which is allosterically deregulated compared to the native plant AGP, accumulated 35% more starch than controls. See Stark, et al., "Regulation of the Amount of Starch in Plant Tissues by ADP Glucose Pyrophosphorylase"; *Science;* Vol. 258; pp. 287–292; (1992); incorporated herein in its entirety by reference. Furthermore, allosteric modification of the maize native Sh2 gene can increase seed weight, presumably due, at least in part, to an effect on starch deposition. See Giroux, et al., "A Single Gene Mutation that Increases Maize Seed Weight"; *Proc. Nat'l. Acad. Sci.;* Vol. 93; pp. 5824–5829; (1996); incorporated herein in its entirely by reference. Allosteric variants of AGP, which are less responsive to 3-PGA and Pi occur naturally in plants. See Kleczkowsi, et al., "Insensitivity of Barley Endosperm ADP-glucose Pyrophosphorylase to 3-phosphoglycerate and Orthophosphate Regulation"; *Plant Physiol.;* Vol. 101; pp. 179–186; (1993); incorporated herein in its entirety by reference. These variants can also be engineered into plants through gene manipulation and plant transformation.

As mentioned above, the reduction of ADP-glucose pyrophosphorylase activity in the cell, plastidic and/or cytoplasmic, (Kim, et al., "Immunocytochemical Localization of ADP-glucose Pyrophosphorylase in Developing Potato Tuber Cells"; *Plant Physiol.;* Vol. 91; pp. 217–220; (1989); and Miller, et al., "Intracellular Immunolocalization of Adenosine 5'-diphohosphoglucose Pyrophosphorylase in Developing Endosperm Cells of Maize (*Zea mays* L.); *Planta;* Vol. 197; pp. 522–527; (1995); incorporated herein in their entirety by reference) will also lower starch synthesis. This can be accomplished by the absence or reduced function of either of two subunits which normally interact to form the active, holoenzyme. However, this enzyme may also be exploited by way of its allosteric properties. ADP-glucose pyrophosphorylase activity is inhibited by Pi. If the subunit(s) of the enzyme are rendered more sensitive to Pi through molecular and protein engineering, then expression of this gene would produce a protein which competes with the native subunit to form a holoenzyme. The activity of ADP-glucose pyrophosphorylase could be reduced proportionally to that fraction of holoenzyme which contains the subunit rendered more sensitive to Pi.

(E) Modification of a Protein Involved in Nucleating Starch Biogenesis

A protein, amylogenin, is believed to serve a nucleating role in the synthesis of the glucosyl polymer. Singh, et al., "β-glucosylarginine: a New Glucose-protein Bond in a Self-glucosylating Protein from Sweet Corn"; *FEBS Lett.;* Vol. 376; pp. 61–64; (1995); incorporated herein in its entirety by reference. Starch synthesis can also be diminished by attaching the initiatior system which primes the glucose polymerization process. A self-glucosylating protein is believed to act in a nucleating function for the biogenesis of starch molecules. See Ardila, et al., "Potato Tuber UDP-glucose: Protein Transglucosylase Catalyzes its own Glucosylation"; *Plant Physiol.;* Vol. 99; pp. 1342–1347; (1992); and Singh, supra both incorporated herein their entirety by reference. Such is the case in glycogen biogenesis. See Lomako, et al., "A Self-glucosylating Protein is the Primer for Rabbit Muscle Glycogen Biosynthesis"; *FASEB Journal;* Vol. 2; pp. 3097–3103; (1988); incorporated herein in its entirety by reference. Elimination of this protein, or formation of a non-functional homolog and expression in the cells leads to interruption of starch biosynthesis and increased accumulation of oil.

(F) Modification of a Protein Responsible for Transport of Assimilates Which Channel into Starch Biosynthesis Proteins involved in assimilate transport, such as the Brittle-1 protein of maize endosperm amyloplast membranes, sucrose carrier proteins or others homologous to the hexose transporter of the chloroplast can also affect starch synthesis by restricting the availability of substrates for normal starch and/or sugar metabolism. See Cao, et al., "Bt1, a Structural Gene for the Major 39–44 kDa Amyloplast Membrane Polypeptides"; *Plant, Cell and Environment;* Vol. 18; pp. 1019–1026; (1995); and Weig, et al., "An Active Sucrose Carrier (Scr1) that is Predominantly Expressed in the Seedlings of *Ricinus Communis L.,*" *Journal of Plant Physiology;* Vol. 147(6); pp. 685–690; (1996); both incorporated herein in their entirety by reference.

The present proteins may also be targeted for disruption of starch synthesis. Included are proteins serving as transporters of intermediates upon which starch synthesis depends. Absence of the Brittle-1 protein in maize causes a severe reduction in starch deposition within the endosperm. This protein acts to transport sugar nucleotide molecules into the amyloplast where starch is made. See Boyer, et al., "Kernel Mutants of Corn"; *Specialty Corns;* A Hallauer, Boca Raton CRC Press, Inc.; pp. 1–28; (1994); and Shannon, et al., "Nucleotides and Nucleotide Sugars in Developing Maize Endosperms-Synthesis of ADP-glucose in Brittle-1"; *Plant Physiology;* Vol. 110(3); pp. 835–843; (1996); both incorporated herein in their entirety by reference.

Knock-out of the Brittle-1 homolog in maize germ or dicotyledonous plants, for example, could result in a similar interruption of starch synthesis in these tissues.

(G) Elimination of Gene Action and Starch Deposition Through Mutation

Restriction of starch biosynthesis in an oil-bearing organ may be achieved in many ways. One may select for a mutant that produces less starch in the tissue of interest, assuming that the tissue is normally enriched in oil. Such mutants can be generated in seed in many ways known to the skilled artisan, such as chemical mutagenesis, x-ray-induced mutagenesis, transposon-induced mutagenesis or mutagenesis by natural means. See Denyer, et al., "The Isolation and Characterization of Novel Low-Amylose Mutants of *Pisum sativum L.*"; *Plant, Cell and Environment;* Vol. 18; pp. 1019–1026; (1995); incorporated herein in its entirety by reference. Mutants which produce less starch can be identified by different methods known in the art. Oil concentration in such mutants is higher than that found in comparable plant material of a non-mutagenic state.

(H) Enhanced Accumulation of Oil in Oil Bearing Crops

During seed development of commercial oilseeds crops (e.g., canola, soybean and sunflower) soluble sugars and starch are significant constituents of the developing cotyledons. For example, it has been shown with sunflowers grown in the field that starch concentration in developing seed can be between 5 and 23% of dry matter. See Luthra, et al., "Relationship of Carbohydrate Metabolism with Lipid Biosynthesis in Developing Sunflower (*Helianthus annuus* L.)"; *J. Plant Physiol.;* Vol. 137; pp. 312–318; (1991); incorporated herein in its entirety by reference.

The exact concentration is dependent upon the stage of development, as starch concentration reaches a peak in early to mid-development and then declines to a low level as triacylglycerol accumulation becomes a primary activity in the seed. A similar phenomenon occurs for starch concentration in developing seed of soybean (Yazdi-Samadi, R, Rinne, et al., "Components of Developing Soybean Seeds: Oil, Protein, Sugars, Starch, Organic Acids, and Amino Acids"; *Agronomy Journal;* Vol. 69; pp. 481–486; (1977); incorporated herein in its entirety by reference) and canola (See Norton, et al., "Compositional Changes in Developing Rape Seed (*Brassica napus* L.)"; *Planta Berl.;* Vol. 123; pp. 163–174; (1975); incorporated herein in its entirety by reference. By specific gene inactivation, either by cosuppression or by antisense, of ADP-glucose pyrophosphorylase activity in the cotyledons of these plants, starch accumulation is severely reduced. In turn, carbon is made available for alternate partitioning within the cells of the seed. Because triacylglycerol biosynthesis requires large inputs of carbon assimilates and is an active and primary metabolic function during seed development, carbon assimilates are metabolically shuttled away from starch synthesis and into the enhanced production of oil materials.

Specifically, a construct is produced consisting of a seed specific promoter (e.g., napin, phaseolin, β-conglycinin) linked to the nucleic acid sequence encoding either one of the subunits of a cotyledonary form of ADP-glucose pyrophosphorylase. The construct is built using either sense orientation (co-suppression) or antisense orientation of the ADP-glucose pyrophosphorylase nucleic acid sequence. Transformation of this gene and an appropriate selectable marker into the proper oil-bearing crop plant, such as sunflower, soybean, cottonseed, or canola, ensure the specific inactivation of ADP-glucose pyrophosphorylase activity in a seed specific manner. The result is reduced starch biosynthesis in the seed and an attendant increase in the concentration of oil in the seed.

The invention now being more generally described, it will be more readily understood by reference to the following examples which are included for purposes of illustration only and are not intended to limit the present invention.

EXAMPLES

Example 1- Cloning of AGP1 ADP-Glucose Pyrophosphorylase Gene and Construction of Expression Vectors A full-length cDNA clone corresponding to the AGP1, large subunit of the embryo isoform of ADP-glucose pyrophosphorylase (Giroux, M., B. Smith-White, et al., "The Large Subunit of the Embryo Isoform of ADP Glucose Pyrophosphorylase from Maize"; *Plant Physiol.;* Vol. 108; pp. 1333–1334; 1995; incorporated herein in its entirety by reference), is obtained using the polymerase chain reaction (PCR). A template is prepared by generating first strand cDNA from total RNA isolated from 16 day-old maize kernels. Primers are designed based upon the published sequence of AGP1 and are designated as N12333 (5'-ATCCATCCGTCCCTAGGTGTGCTTCA-3') and N12339 (5'-CGCGCCTCAAACTAAGTCTCAACTCTC-3'). These primers are used in a PCR reaction to amplify the AGP1 cDNA by conventional methods. The resulting PCR product is purified and subcloned into the vector PCRII (Invitrogen) and sequenced on both strands to confirm its identity. This clone is designated p9734. An embryo-specific expression cassette is constructed by digesting p9734 with EcoRl, treating with Klenow enzyme to generate blunt ends, and then gel purifying the resulting approx. 1.6 kb AGP1 cDNA. This is ligated between the globulin-1 (glb1) promoter and terminator sequences of the vector p3303. Extensive restriction enzyme mapping is performed on the resulting clone, p9733, to ensure the AGP1 cDNA is in an antisense orientation relative to the glb1 promoter and terminator sequences. In preparation for maize transformation, p9733 is linked in cis to two separate selectable marker expression cassettes by subsequent ligations with p3528 (2×CAMV::BAR::PinII) and p8092 (Ubi::Pat::35S) to generate plasmids p10000 and p9763, respectively. These plasmids are used in particle bombardment of maize immature embryos.

Example 2- Preparation of Transgenic Plants

The general method of genetic transformation used to produce transgenic maize plants is mediated by bombardment of embryogenically responsive immature embryos with tungsten particles associated with DNA plasmids, said plasmids consisting of a selectable and an unselectable marker gene.

(I) Preparation of Tissue

Immature embryos of "High Type II" are the target for particle bombardment-mediated transformation. This genotype is the $F_1$ of two purebred genetic lines, parent A and parent B, derived from A188×B73. Both parents are selected for high competence of somatic embryogenesis. See Armstrong, et al., "Development and Availability of Germplasm with High Type II Culture Formation Response," *Maize Genetics Cooperation Newsletter*, Vol. 65, pp. 92 (1991); incorporated herein in its entirety by reference.

Ears from $F_1$ plants are selfed or sibbed, and embryos are aseptically dissected from developing caryopses when the scutellum first becomes opaque. The proper stage occurs about 9–13 days post-pollination, and most generally about 10 days post-pollination, and depends on growth conditions. The embryos are about 0.75 to 1.5 mm long. Ears are surface sterilized with 20–50% Clorox for 30 min, followed by 3 rinses with sterile distilled water.

Immature embryos are cultured, scutellum oriented upward, on embryogenic induction medium comprised of N6 basal salts (Chu, et al., "Establishment of an Efficient Medium for Anther Culture of Rice Through Comparative Experiments on the Nitrogen Sources," *Scientia Sinica* (Peking), Vol. 18, pp. 659–668 (1975); incorporated herein in its entirety by reference; Eriksson vitamins (See Ericksson, T., "Studies on the Growth Requirements and Growth Measurements of *Haplopappus gracilis*," *Physiol. Plant*, Vol. 18, pp. 976–993 (1965); incorporated herein in its entirety by reference), 0.5 mg/l thiamine HCL, 30 gm/l sucrose, 2.88 gm/l L-proline, 1 mg/l 2,4-dichlorophenoxyacetic acid, 2 gm/l Gelrite, and 8.5 mg/l $AgNO_3$. The medium is sterilized by autoclaving at 121° C. for 15 min and dispensed into 100×25 mm petri dishes. $AgNO_3$ is filter-sterilized and added to the medium after autoclaving. The tissues are cultured in complete darkness at 28° C. After about 3 to 7 days, most usually about 4 days, the scutellum of the embryo has swelled to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per petri dish are located in the center of a petri dish in an area about 2 cm in diameter. The embryos are maintained on this medium for 3–16 hr, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 μl are deposited on macrocarriers and the ethanol allowed to evaporate. The macrocarrier is accelerated onto a stainless-steel stopping screen by the rupture of a polymer diaphragm (rupture disk). Rupture is effected by pressurized helium. Depending on the rupture disk breaking pressure, the velocity of particle-DNA acceleration may be varied. Rupture disk pressures of 200 to 1800 psi are commonly used, with those of 650 to 1100 psi being more preferred, and about 900 psi being most highly preferred. Rupture disk breaking pressures are additive so multiple disks may be used to effect a range of rupture pressures.

Preferably, the shelf containing the plate with embryos is 5.1 cm below the bottom of the macrocarrier platform (shelf #3), but may be located at other distances. To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A petri dish with the target embryos is placed into the vacuum chamber and located in the projected path of accelerated particles. A vacuum is created in the chamber, preferably about 28 inches Hg. After operation of the device, the vacuum is released and the petri dish is removed.

Bombarded embryos remain on the osmotically adjusted medium during bombardment, and preferably for two days subsequently, although the embryos may remain on this medium for 1 to 4 days. The embryos are transferred to selection medium comprised of N6 basal salts, Eriksson vitamins, 0.5 mg/l thiamine HCL, 30 gm/l sucrose, 1 mg/l 2,4-dichlorophenoxyacetic acid, 2 gm/l Gelrite, 0.85 mg/l $AgNO_3$ and 3 mg/l bialaphos. Bialaphos is added filter-sterilized. The embryos are subcultured to fresh selection medium at 10 to 14 day intervals. After about 7 weeks, embryogenic tissue, putatively transformed for both selectable and unselected marker genes, is seen to proliferate from about 7% of the bombarded embryos. Putative transgenic tissue is rescued, and that tissue derived from individual embryos is considered to be an event and is propagated independently on selection medium. Two cycles of clonal propagation is achieved by visual selection for the smallest contiguous fragments of organized embryogenic tissue.

For regeneration of transgenic plants, embryogenic tissue is subcultured to medium comprised of MS salts and vitamins (Murashige, T. and F. Skoog, "A revised medium for rapid growth and bio assays with tobaccotissue cultures"; Physiologia Plantarum; Vol. 15; pp. 473–497; 1962; incorporated herein in its entirety by reference), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm petri dishes and incubated in darkness at 28° C. until the development of well-formed, matured somatic embryos can be visualized. This requires about 14 days. Well-formed somatic embryos are opaque and cream-colored, and are comprised of an indentifiable scutellum and coleoptile. The embryos are individually subcultured to germination medium comprised of MS salts and vitamins, 100 mg/l myo-inositol, 40 gm/l sucrose and 1.5 gm/l Gelrite in 100×25 mm petri dishes and incubated under a 16 hr light:8 hr dark photoperiod and 40 $\mu$Einsteinsm$^2$sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hr light:8 hr dark photoperiod and 40 $\mu$Einsteinm$^{-2}$sec$^{-1}$ from cool-white fluorescent tubes. After about 7 days, the plants are well-established and are transplanted to horticultural soil, hardened off and potted into commercial greenhouse soil mixture and grown to sexual maturity in a greenhouse. An elite inbred line is used as a male to pollinate regenerated transgenic plants.

(J) Preparation of Particles

Fifteen mg of tungsten particles (General Electric), 0.5 to 1.8 $\mu$m preferably 1 to 1.8 $\mu$m, and most preferably 1 $\mu$m, are added to 2 ml of concentrated nitric acid. This suspension is sonicated at 0° C. for 20 min (Branson Sonifier Model 450, 40% output, constant duty cycle). Tungsten particles are pelleted by centrifugation at 10,000 rpm (Biofuge) for 1 min and the supernatant is removed. Two ml of sterile distilled water is added to the pellet and sonicate briefly to resuspend the particles. The suspension is pelleted, 1 ml of absolute ethanol is added to the pellet and sonicated briefly to resuspend the particles. Rinse, pellet, and resuspend the particles a further 2 times with sterile distilled water, and finally resuspend the particles in 2 ml of sterile distilled water. The particles are subdivided into 250 $\mu$l aliquots and stored frozen.

(K) Preparation of particle-plasmid DNA association

The stock of tungsten particles is sonicated briefly in a water bath sonicator (Branson Sonifier Model 450, 20% output, constant duty cycle) and 50 $\mu$l is transferred to a microfuge tube. Plasmid DNA is added to the particles for a final DNA amount of 0.1 to 10 $\mu$g in 10 $\mu$l total volume, and briefly sonicated. Preferably 1 $\mu$g total DNA is used. Specifically, 10 $\mu$l of P9764 (ubi$_p$::ubiint::MO-PAT::CaMV35s$_t$+glb1$_p$::anti-AGP1::glb1$_t$) or 10 $\mu$L of P9763 (CaMV35s$_t$::MO-PAT::ubiint::ubi$_p$+glb1$_p$::anti-AGP1::glb1$_t$), at 0.1 $\mu$g/$\mu$l in TE buffer, are added to the particle suspension. Fifty $\mu$l of sterile aqueous 2.5 M CaCl$_2$ are added, and the mixture is briefly sonicated and vortexed. Twenty $\mu$l of sterile aqueous 0.1 M spermidine are added and the mixture is briefly sonicated and vortexed. The mixture is incubated at room temperature for 20 min with intermittent brief sonication. The particle suspension is centrifuged, and the supernatant is removed. Two hundred fifty $\mu$l of absolute ethanol is added to the pellet and briefly sonicated. The suspension is pelleted, the supernatant is removed, and 60 $\mu$l of absolute ethanol is added. The suspension is sonicated briefly before loading the particle-DNA agglomeration onto macrocarriers.

Example 3- Analysis of Seed from Transgenic Corn Plants

A sample of tissue from each event is processed to recover DNA The DNA is probed with primer sequences designed to amplify DNA sequences overlapping the glb1 promoter and the AGP1 portion of the plasmid and/or the glb1 terminator and the AGP1 portion of the plasmid. Embryogenic tissue with amplifiable sequence is advanced to plant regeneration.

Seed of mature ears from transgenic plants shown to be PCR positive are harvested and dried to a similar moisture concentration of approximately 12%. Starch, protein and oil concentration in the whole grain are measured by near infrared transmittance to determine whether whole grain compositional quality has be affected by antisense inhibition of AGP1 in the germ.

More critical determination of how antisense expression of AGP1 in the germ impact seed metabolism and chemical composition is conducted by studies involving isolated germs. Seed is harvested at approximately 25 days after pollination (DAP) and germ isolated by dissection. The activity of ADP-glucose pyrophosphoylase (ATP:D-Glc-1-phosphate adenyltransferase, EC 2.7.7.27) is measured in isolated, fresh, diced embryos by extraction (4° C.; Virtis-hear Homogenizer, 25,000 rpm, 20 sec) in buffer [1:10 wt/vol; 50 mM Hepes-NaOH (pH 7.5), 5 mM MgCl$_2$, 1 mM DTT, 1 mg/mL BSA]. The homogenate is centrifuged (30,000×g, 15 min, 4° C.) and the supernatant assayed for activity as described in Singletary, et al., "Nitrogen-induced Changes in the Growth and Metabolism of Developing Maize Kernels Grown in vitro," *Plant Physiol.*, Vol. 92, pp. 160–167, (1980); incorporated herein in its entirety by reference. The supernatant, is also run on 4–20% SDS-PAGE gels and blotted to nitrocellulose. A Western assay for detection of AGP1 protein, is conducted using an antibody produced against a portion of the AGP1 protein. Methods for blotting and western development are followed according to recommendations of Bio-Rad (Hercules, Calif.).

Germs are isolated from mature kernels for determination of starch and oil concentrations of the seed part. Individual dry seed are soaked overnight at 4° C. in 1 mL of solution containing 20 mM acetate (pH 6.5) and 10 mM mercuric chloride. (Adkins, G. K. and C. T. Greenwood, "The Isolation of Cereal Starches in the Laboratory"; *Starch;* Vol. 7; pp. 213–218; 1966). Intact germ is dissected from the seed, dried by lyophilization and recorded for dry weight. Individual germ is ground for 10 sec in a Silamet amalgam mixer and transferred with hexane washing into a microcentrifuge tube. The tissue is extracted by stirring with 1 mL of hexane 3×60 min and centrifuged after each extraction period. The supernatant of extractions is collected and placed into a preweighed aluminum pan. After evaporation of hexane from the weigh pans in a fumehood, final traces of solvent are removed in a forced draft oven at 105° C. for 15 minutes. Cooled weigh pans are reweighed to determine the total weight of oil extracted from the germ. The meal remaining after oil extraction is twice washed with water and centrifugation (10 min; 1,000×g) and analyzed for starch by a modified procedure for total starch measurement (McCleary, B. V., V. Solah, et al., "Quantitative Measurement of Total Starch in Cereal Flours and Products"; *Journal of Cereal Science;* Vol. 20; pp. 51–58; 1994). Free sugars are removed by extraction with 80% ethanol and the starch dissolved in 90% dimethylsulfoxide. Heat stable $\alpha$-amylase and high purity amyloglucosidase (very low in $\beta$-glucanse activities) are used to degrade the starch to monomeric carbohydrate. The resulting glucose will be quantitated according to (Jones, M. G. K., W. H. Outlaw, et al., "Enzymic Assay of $10^{-7}$ to $^{-14}$ Moles of Sucrose in Plant Tissues"; *Plant Physiol.*; Vol. 60; pp. 379–383; 1977) with modification to a microplate format.

We claim:

1. A method for enhancing the accumulation of oil beyond normal levels in the embryo of seed of a corn plant and not in other tissues, the method comprising reducing starch production by diminishing or abolishing the activity of ADP-glucose pyrophosphorylase in the embryo and not in other tissue.

2. A method according to claim 1 wherein the seed is further characterized in that the size of the oil storage organ is not significantly affected.

3. A method according to claim 1 wherein the plant is a cereal plant and the enhanced accumulation of oil is not accompanied by a reduction in endosperm size.

4. A seed produced by the method of claim 1.

5. A seed produced by the method of claim 2.

6. A seed produced by the method of claim 3.

* * * * *